United States Patent
Stett et al.

(10) Patent No.: US 7,361,500 B2
(45) Date of Patent: Apr. 22, 2008

(54) APPARATUS AND METHOD FOR ELECTRICALLY CONTACTING BIOLOGICAL CELLS SUSPENDED IN A LIQUID

(75) Inventors: Alfred Stett, Reutlingen (DE); Wilfried Nisch, Tübingen (DE); Hugo Hämmerle, Tübingen (DE); Thomas Knott, Wankheim (DE)

(73) Assignee: Cytocentrics AG, Rostock (DE)

( * ) Notice: Subject to any disclaimer, the term of this patent is extended or adjusted under 35 U.S.C. 154(b) by 0 days.

(21) Appl. No.: 10/337,059

(22) Filed: Jan. 3, 2003

(65) Prior Publication Data

US 2003/0153067 A1    Aug. 14, 2003

Related U.S. Application Data

(63) Continuation of application No. PCT/EP01/07713, filed on Jul. 5, 2001, now abandoned.

(30) Foreign Application Priority Data

Jul. 5, 2000    (DE)    ............ 100 32 568

(51) Int. Cl.
*C12M 1/42* (2006.01)
(52) U.S. Cl. ............ 435/285.2; 435/287.1; 435/288.5
(58) Field of Classification Search ........... 435/29, 435/30, 459, 461, 470, 173.4–173.6, 285.1, 435/285.2, 287.1, 287.2, 288.5, 293.1; 436/63
See application file for complete search history.

(56) References Cited

U.S. PATENT DOCUMENTS 6,193,647 B1 *  2/2001  Beebe et al. ............ 600/33
6,315,940 B1    11/2001 Nisch et al.
6,368,851 B1 *  4/2002  Baumann et al. ........ 435/285.2

FOREIGN PATENT DOCUMENTS

| DE | 197 12 309 A 1 | 5/1998 |
| DE | 198 27 957 A 1 | 12/1999 |
| WO | WO 9822819 A1 * | 5/1998 |
| WO | WO 200020554 A1 * | 4/2000 |
| WO | WO 00/34776 | 6/2000 |

OTHER PUBLICATIONS

Neher et al., "The Patch Clamp Techniques," *Scientific American*, Mar. 1992, pp. 28-35.

* cited by examiner

*Primary Examiner*—William H. Beisner
(74) *Attorney, Agent, or Firm*—Knobbe Martens Olson & Bear LLP

(57) ABSTRACT

An apparatus for electrically contacting biological cells suspended in a liquid has a substrate having at least one opening and an electrode for electrically contacting a cell immobilized above the opening. A contact unit with a contact tip is arranged below said opening. A top end of the contact tip projects into the opening in such a way that it comes to bear against a cell membrane of the immobilized cell. The contact tip has a contact channel which ends at its top end. A hydrodynamic low pressure can be exerted upon the cell membrane via the contact channel, and the electrode is electrically connected to the contact channel. In a method for electrically contacting biological cells suspended in a liquid, a cell is immobilized above an opening provided in a substrate, and the immobilized cell is contacted via at least one electrode. For contacting the immobilized cell, a hydrodynamic low pressure is generated acting on a cell membrane through a contact tip projecting into the opening.

10 Claims, 7 Drawing Sheets

APPARATUS AND METHOD FOR ELECTRICALLY CONTACTING BIOLOGICAL CELLS SUSPENDED IN A LIQUID

CROSS-REFERENCES TO RELATED APPLICATIONS

This application is a continuation of international patent application PCT/EP01/07713 filed on Jul. 5, 2001, published in German and designating the U.S., now abandoned, which claims priority from German patent application DE 100 32 568.8, filed on Jul. 5, 2000.

BACKGROUND OF THE INVENTION

The present invention relates to an apparatus for electrically contacting biological cells suspended in a liquid, and more particularly to an apparatus comprising a substrate having at least one opening, a means for immobilizing a cell on the opening, and at least one electrode for electrically contacting the immobilized cell.

The invention further relates to a method of electrically contacting biological cells suspended in a liquid, comprising the steps of immobilizing a cell above an opening provided in a substrate, and contacting the immobilized cell via at least one electrode.

An apparatus known from DE 197 12 309 A1 (which is equivalent to U.S. Pat. No. 6,315,940 assigned to the present assignee and which is incorporated here by reference) comprises a microelectrode arrangement in which the cells are captured in microcuvettes at the bottom of which an electrode is located. The electrode is provided with a central suction channel in which a low pressure can be generated by connecting channels which run underneath the electrodes. Thus, it is possible to attract individual cells selectively to the electrodes and immobilize them on the electrodes with a certain contact pressure. It is feasible to use the known apparatus for measurements on cells, but only from the outside of their cell membranes.

Microelectrode arrangements of this kind are generally used for studying biological cells. The microelectrode arrangements serve, for example, to stimulate the cells or to pick up cell potentials. The studies may be carried out in a biological environment or in an artificial environment. In conventional microelectrode arrangements, however, it depends more or less on chance whether or not one or another cell settles on a particular electrode. Furthermore, the cells generally settle on an electrode only with partial coverage, so that stimulating the cell or picking up a cell potential is limited to this partial area.

Although the apparatus known from DE 197 12 309 A1 already mentioned above removes most of these disadvantages, in particular by ensuring that only one cell settles on any micro-electrode, it is nevertheless still a matter of chance as to whether a cell and which cell is captured in the microcuvette. Furthermore, it cannot be ruled out that particles present in the liquid are sucked into the microcuvette, which do allow a measurement to be carried out, although its results are unusable.

Another characteristic of the known apparatus and the known method is the fact that measurements can be carried out only on the outside of the cell membranes. Intracellular measurements are not possible.

Intracellular measurements, however, can be carried out using the well known "patch clamp" technique in which a "membrane patch clamp" is used; see, for example, Neher and Sakmann: "Die Erforschung von Zellsignalen mit der Patch-Clamp-Technik", Spektrum der Wissenschaften, May 1992, p. 48.

In this technique, a micropipette filled with electrically conductive liquid is selectively brought close to an adherent cell and is lowered down onto the membrane thereof which, as a result, bulges slightly inward. The membrane patch enclosed by the pipette tip is then sucked in slightly by means of low pressure, thereby sealing off and electrically isolating the membrane patch from the surrounding liquid. This isolation is often referred to as gigaseal.

In this way it is possible to carry out, for example, measurements of ion channels on the outside of a membrane.

However, if the sealed-off membrane is sucked in further, the membrane patch is perforated so that there is access through the pipette orifice to the cell interior, which is sealed off hydrodynamically and electrically from the surrounding liquid, making intracellular measurements and stimulations possible ("whole cell patch").

However, the patch clamp technique can only be carried out on adherent or otherwise immobilized cells, which the fragile glass pipette has to be brought close to by means of a micro-manipulator in each case. For this reason, the number of simultaneously contactable cells is extremely limited so that a plurality of cells can be processed only sequentially.

Therefore, this method is unsuitable for mass studies, as would be required, for example, in the area of drug screening, substance screening, etc.

Another disadvantage of the conventional patch clamp technique is the fact that it cannot be automated but is carried out manually by workers who need to have a lot of experience and manual skills.

From DE 198 27 957 A1, it is know to immobilize a cell on a glass support whose surface has a ring structure-like profile in order to improve cell adhesion. A conically projecting electrode whose sharp, ring-shaped tip cuts into the cell membrane is arranged on the glass support in the cell-supporting area. The known apparatus, however, has the disadvantage that the electrical sealing on the ring-shaped electrode tip is determined only by the "adhesive force" of the cell on the profiled surface.

SUMMARY OF THE INVENTION

It is an object of the present invention to improve a method and an apparatus of the kind mentioned at the beginning so as to avoid the abovementioned disadvantages. In particular, it is an object to provide an efficient and universal approach for electrically contacting cells. It is furthermore an object to provide an approach for electrically contacting cells which approach can easily be automated in order to con-duct mass studies. It is another object to provide an approach which basically allows to carry out measurements either on the outside of the cell membrane and/or intracellularly.

According to one aspect of the invention, this object is achieved by a contact unit arranged at the opening, the contact unit having a contact tip whose top end projects into the opening so as to come to bear against the cell membrane of an immobilized cell, said contact tip having a contact channel which ends at its top end and via which a hydrodynamic low pressure can be exerted on the cell membrane, wherein the electrode is in electrical contact with the contact channel.

According to another aspect of the invention, this object is achieved by exerting a hydrodynamic low pressure on the cell membrane through a contact tip projecting into the opening in order to contact the immobilized cell, with the electrode coming to contact the cell electrically through the contact tip, and said immobilization causing the cell to press against the contact tip.

According to yet another aspect of the invention, the cell may be immobilized by a first immobilizing force and the electrical contact is achieved using a hydrodynamic low pressure exerted upon the cell membrane through a contact channel which itself is in electrical contact with an electrode. The immobilizing force is preferably achieved by means of a second low pressure for sucking in the cell and/or by a functional coating, which, even more preferable, is selective for the cell.

Immobilization of the cells on the contact tip here simultaneously causes the cell membranes to bulge inward. The means for immobilization, preferably the low pressure in the suction channel, thus cause, in addition to immobilization, a contacting between cell membrane and contact tip and further cause the cell membrane to exert pressure on the contact tip. A patch clamp-like tip may project into the opening, via which tip electrical signals can be measured and/or applied either on the outside of the membrane and/or intracellularly. The adhesive pressure caused by the means for immobilization is independent of and separate from the contact pressure so that the contact tip diameter can be very small, making possible a reliable gigaseal and good perforation. The diameter of the opening is distinctly larger than the diameter of the contact tip, resulting in a very high adhesive pressure, without the cell being sucked into the suction channel or even into the contact channel.

In this way stable long-term measurements are also possible with perfusion where substances flow along the outside of the cell in order to cause particular cellular reactions which are again to be recorded via the electrode.

Since the contact tip projects into the opening, sucking the cell onto the opening by means of the suction channel causes the cell membrane in the area of the contact tip to bulge inward, as is also desirable in the manual patch clamp technique in order to provide a good gigaseal, when a slightly low pressure is exerted on the membrane patch through the con-tact channel. It is then possible, by increasing the low pressure in the contact channel in the form of short-term pulses, to perforate the membrane patch in a reproducible manner known per se.

The inventors of the present application have found that the separation of suction channel and contact channel enables reliable and thus automated positioning of cells above the opening and contacting thereof following the patch clamp technique.

In a refinement of the apparatus, preference is given to the contact unit being arranged at the opening in a detachable manner, and further preference is given to the contact tip being arranged in a replaceable manner.

Advantageously, it is possible here to easily replace the contact unit and/or the contact tip, while the other components of the novel apparatus are reusable. This measure is based on the finding that patch clamp tips can be used only once, and, after only a second use, the gigaseal is no longer sufficient and membrane perforation is no longer reliable.

In this connection, preference is given to the suction channel running inside the substrate, while it is also preferable, on the other hand, for at least some sections of the suction channel to run inside the contact unit.

If the suction channel runs inside the substrate, the possibility of constructing the contact unit in a very simple and inexpensive manner is advantageous. If, however, some sections of the suction channel run inside the contact unit, the exterior connection of both the suction channel and the contact channel may be carried out in a simple manner at the contact unit itself, thereby simplifying handling and construction.

Further preference is given to the contact unit having a replaceable top part containing the contact tip and a reusable bottom part containing the electrode and a first section of the contact channel, with the contact unit preferably resting against the outside of the substrate in the region of the opening and sealing said opening on the outside in a liquid-tight manner, and the top part further preferably resting with pressure against the outside of the substrate and the bottom part resting with pressure against the top part.

These measures have the advantage that, in order to re-place the contact tip, only the top part of the contact unit has to be replaced. Since bottom part and top part rest with pressure against each other and against the substrate, screwing or similar manipulations are not necessary, and the replacement can be carried out in an automated and simple manner, for example with the aid of a micromanipulator.

In this connection, preference is given to a sealant being provided between the substrate and the top part and/or between the top part and the bottom part, which sealant is preferably being selected from the group of: silicone paste, two-component elastomer and polydimethylsiloxane elastomer (Sylgard™).

This measure has the advantage that good, liquid-tight sealing between substrate, top part and bottom part takes place even with a small pressure, so that there are lower demands to be made on the micromanipulator, both with respect to accuracy and with respect to exerting pressure, than if, for example, a washer were to be used for sealing.

Further preference is given to providing, in the bottom part, a chamber into which the electrode projects and in which the first section of the contact channel ends.

Here, the electrode and the first section of the contact channel are advantageously arranged in the reusable bottom part so that the cost for carrying out a measurement is determined only by the replaceable top part which carries merely the con-tact tip and a second section of the contact channel.

In this connection, preference is given to a funnel-shaped second contact channel section which is attached to the chamber and runs through the contact tip being arranged in the top part.

Further preference is given to a ring being located between the top part and the substrate around the contact tip, which ring has, in the direction of the bottom part, an aperture which is connected to a first section of the suction channel in the bottom part.

In this simple manner, the suction channel can be integrated into the contact unit. The suction channel then runs from the bottom part via the aperture into the annular space around the contact tip and sucks the cell onto the opening and against the contact tip there. It is here furthermore advantageous that only a very simply constructed top part which can be produced, like all other components, by microsystems technology, i.e. in a microstructured form, needs to be replaced.

In a refinement, preference is given to the annular space being sealed in the direction of the substrate with a membrane in which a gap surrounding the contact tip at a distance is provided.

Here, the opening in the substrate can advantageously be distinctly larger than the gap through which the suction channel sucks the cell onto the opening. In this way, lesser demands need to be made on the manipulation accuracy of the micromanipulator, since it only needs to be ensured that the gap is arranged in the region of the opening; sealing toward the outside is effected by the membrane which is advantageously fixed to the top part.

In general, preference is given to a reference electrode projecting into the liquid in the region of the opening.

Advantageously, this measure makes it possible to measure very reliably and reproducibly potentials on the cell membrane or intracellularly, due to the spatial proximity of electrode and reference electrode.

In general, preference is given to providing a functional coating on the substrate around the opening, as a means for immobilizing the cells.

This measure advantageously serves for selecting the cells to be contacted. For a generic apparatus and a generic method, said measure is novel and inventive, even on its own. Using a functional coating makes it possible now to select and contact a particular type of cell from a suspension of different cells. Only those cells which are immobilized on the functional coating adapted to the cells themselves are also used for measurement.

In this connection, the functional coating is preferably selected from the group of: polyanions; polycations; polyethyleneimine; antibodies against cell surface molecules such as integrins (e.g. fibronectin) or lectins; and magnetic coating.

By choosing polyanions, polycations and polyimines appropriate chemical immobilization can be provided, while immobilizing by suitable antibodies in the functional coating can produce a specificity for any desired cell surface molecules.

If the functional coating comprises a magnetic coating, it is possible to capture in this way magnetic antibodies which have been added to the cell suspension previously and have attached to particular cell surface molecules. Choosing a specific magnetic antibody makes it possible to immobilize cells from the cell suspension, which can be predetermined accurately in this manner. Antibodies coupled to magnetic particles are known in the prior art and are sold, for example, by Per Septive Diagnostics Incorporated, Cambridge, Mass.; see Ahern: Antibodies Making Their Way from the Clinic to the Research Lab", The Scientist, Volume 9, 1995, pp. 18-19.

The means for immobilizing, such as the suction channel, further have the effect that the immobilization itself results in contact between cell membrane and contact tip and that a force directed toward the contact tip is exerted on the cell membrane.

In this connection, preference is further given to providing a positioning unit in order to position a cell above the opening, which positioning unit may comprise laser tweezers, may build up an electromagnetic field or may generate a hydro-dynamic force.

Thus, on the one hand, the positioning unit may be represented just by the suction channel which generates a hydrodynamic force, or else, independently of the suction channel or in addition to the suction channel, laser tweezers or an electromagnetic field, for example, may be provided.

Laser tweezers are well known in the prior art, and these optical tweezers are optical manipulators which are based on the law of momentum conservation.

An object which is substantially transparent for laser light hardly absorbs any energy but deflects the beam from the original direction according to the law of refraction. This refraction imparts to the cell an impulse which moves said cell. In this way a pair of symmetric laser beams forms a trap in which the cell is held. The cell can be moved by moving the beams; see Berns: "Mit Laserwerkzeugen ins Zellinnere", Spektrum der Wissenschaften, July 1998, p. 56.

By means of the positioning unit it is possible, for example, to place a cell on the functional coating. If, thereafter, said positioning unit releases the cell, the latter remains above the opening only if it can be immobilized by the functional coating. This makes it possible to select cells in a simple manner. If the cell is moved on by the transport flow in the apparatus after having been released by the positioning unit, a negative selection has been made; otherwise, the selection is positive.

In this way it is possible to pick from a suspension of different cells specifically those cells which are to be contacted with the apparatus. This selection, too, in a generic apparatus and a generic method, is novel and inventive per se.

In this connection, preference is given to the substrate being arranged in a flow channel, preferably being an integral component of a wall of a flow channel through which the liquid is directed to the opening with a defined and/or adjustable transport flow, and preferably a sensor unit is provided which reacts to a parameter of the cell and controls the positioning unit and/or the suction channel.

The substrate may be, for example, in a position perpendicular to the wall of the flow channel and thus perpendicular to the flow which can thus flow directly against it.

The sensor unit also serves to select cells and, like the functional coating, is novel and inventive per se in a generic apparatus and a generic method.

In this connection, the parameter is selected from the group of: optical parameters such as fluorescence, absorption, reflection, diffraction, refraction; geometric parameters such as size, length, diameter, shape; electrical parameters such as capacity, resistance; and biological, chemical and physical cell parameters.

The sensor unit is preferably arranged upstream of the opening.

The sensor unit makes it possible to select cells, in particular in connection with the adjustable transport flow and/or the positioning unit. If the sensor unit recognizes, on the basis of the measured cell parameters, a cell to be contacted, this is relayed to the positioning unit and/or the suction channel which then act according to the known transport flow set at that time when the cell selected by the sensor unit is in their area. It is also possible to provide a further sensor unit just upstream of the suction channel, which serves to locate a cell and reports the location thereof at that moment to the suction channel and/or the positioning unit.

The sensor unit and the optionally provided further sensor unit thus make possible a distinctly more efficient selection of cells than the functional coating, and the combination of sensor unit(s), positioning unit and functional coating makes possible a very stringent selection of the cells to be contacted.

In general, preference is given to arranging a microperfusion unit upstream of the opening, in order for test substances to flow around an immobilized cell, with the components of the apparatus preferably being produced using microsystems technology.

In this way it is possible for small amounts of substances to flow to the immobilized cell, giving the possibility of cost-effective operation.

In the novel method, preference is given to replacing the contact tip prior to each contacting.

It is advantageous here to use a new contact tip for each new contacting, ensuring reliable formation of a gigaseal and reliable perforation of the enclosed membrane patch, if this is desired.

Preference is furthermore given to directing the liquid with adjustable transport flow through a channel to the opening.

Here, the suspended cells float past the opening in a known time sequence so that a process control can address the suction channel in each case at the right time.

Preference is further given to immobilizing the cell by adhering to a functional coating which is arranged on the substrate around the opening, with a positioning unit preferably positioning the cell above the opening and, more preferably, prior to positioning a cell, measuring a parameter of said cell and selecting the cell for positioning depending on said parameter.

Advantageously, there is no need here to work with totally pure cell populations, but rather it is also possible to select desired cell types from mixed cell suspensions for contacting.

In this connection, preference is given to selecting a cell by positioning it on the functional coating by means of the positioning unit which then releases it, so that only those cells which are attached to the functional coating remain immobilized.

It is advantageous here that in principle any cell floating past the positioning unit is tested via the functional coating as to whether it should be contacted or else can be released.

In this connection, preference is given to immobilizing the cell by hydrodynamic low pressure, in addition to the functional coating.

This measure has the advantage of a reliable adhesive force on a cell selected via the functional coating being selected so that it is possible to arrest said cell securely during a long-term measurement, for example by means of perfusion.

Finally, preference is also given to removing the cell from the opening by increasing the low pressure applied for immobilization to a high pressure.

Advantageously, it is possible here to actively push off the cell again, after the end of a measuring and stimulation phase.

In summary, the novel apparatus and the novel method thus offer the possibility to select individual cells from a suspension according to at least one criterion, i.e. a cell parameter, and to position and immobilize the selected individual cells from the suspension on a measurement site, i.e. at the opening. The immobilization is carried out here either via a suction channel, i.e. using hydrodynamic low pressure, and/or via a functional coating.

According to the method of the classical patch clamp technique, the cell is sucked in by the contact channel for the purpose of forming a high-resistance seal, while it is possible here to perforate the sucked-in and sealed membrane optionally by means of a pressure pulse.

The immobilized and contacted cell may be perfused with liquids containing test substances so that it is possible to carry out serial studies on a multiplicity of cells in an automated manner, utilizing at the same time the advantages of the classical patch clamp technique.

Further advantages can be seen from the description and the attached drawing.

It is obvious that the features mentioned above and still to be illustrated below can be used not only in each of the combinations stated but also in other combinations or on their own, without leaving the scope of the present invention.

BRIEF DESCRIPTION OF THE DRAWINGS

Exemplary embodiments of the invention are depicted in the drawing and will be illustrated in more detail in the following description in which.

DETAILED DESCRIPTION OF THE PREFERRED EMBODIMENT

Figure 1:
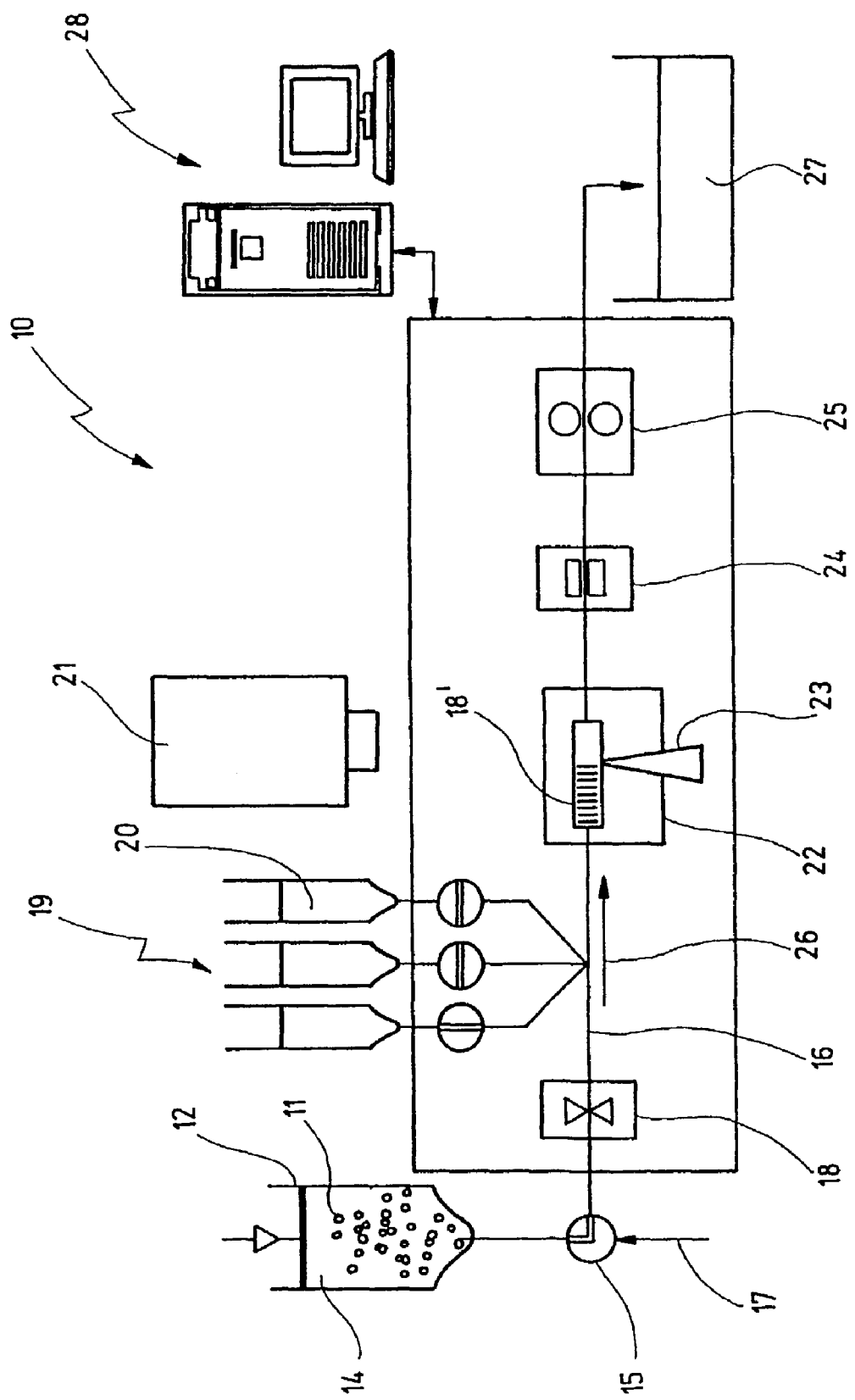
FIG. 1 depicts a diagrammatic overview of the novel apparatus.

In FIG. 1, reference number 10 indicates an apparatus for electrically contacting cells 11 which are suspended in a liquid 14 stored in a reservoir 12.

The reservoir 12 is connected with a switching valve 15 through which the liquid 14 is passed into a flow channel 16 in which the cells 11 are electrically contacted in a manner still to be described.

An inlet 17 for a washing solution is also connected to the switching valve 15 so that, after a cell 11 has been analyzed, the flow channel 16 can be flushed with said washing solution.

Alongside the flow channel 16, firstly a sensor unit 18 is arranged via which the parameters of the cells 11 are measured.

The sensor unit 18 is followed by a microperfusion unit 19 via which the perfusion solutions 20 can be introduced into the flow channel 16 in order to perfuse a contacted cell, i.e. for test substances to flow at said cell.

The microperfusion unit 19 is followed by a positioning unit 21 via which the cells 11 can be positioned in a contacting and measuring unit 22 and immobilized there.

The positioning unit 21 is controlled, for example, depending on output signals of the sensor unit 18.

FIG. 1 further indicates a conventional patch clamp tip 23 in the contacting and measuring unit 22, via which it is possible to automatically carry out measurements on the outside of a membrane of the cell 11, and also intracellular measurements in a manner still to be described.

Upstream of the patch clamp tip 23, a further sensor unit 18' may be arranged which, in the exemplary embodiment shown in FIG. 1, is arranged in the contacting and measuring unit 22. The further sensor unit 18' can locate individual cells in the flow channel 16 via optical and other methods and control the sucking-in of said individual cell via its measuring channel, as is yet to be described in detail further below.

While the sensor unit 18 serves to select a cell to be sucked in, the further sensor unit 18' has the task of locating an individual cell and determining the location thereof at that moment in such a way that said cell can be contacted with the patch clamp tip 23 via the positioning unit 21 and/or by sucking-in.

The contacting and measuring unit 22 is followed by a second sensor unit 24 which in turn is followed by a control 25 for a transport flow of the liquid 14 in the flow channel 16, which flow is indicated at 26. Finally, the flow channel 16 ends in a container 27 for collecting liquid 14 and washing solution 17.

Finally, FIG. 1 also depicts a process control and data processing 28 via which the individual components of the apparatus are controlled and functionally linked to one another.

The transport flow 26 is adjusted via the process control and data processing 28 in such a way that in each case a single cell flows past the sensor unit 18, is analyzed there with respect to particular parameters and then, if selected by the positioning unit 21, is positioned in the contacting and measuring unit.

The positioning unit 21 may be, for example, laser tweezers or else may build up an electromagnetic field via which antibodies which are coupled to magnetic particles and which are located on the surface of the cells 11 are transported to the measuring site.

In addition, it is also possible to provide a hydrodynamic low pressure for immobilizing a cell 11, instead of or in addition to the positioning unit 21, in the contacting and measuring unit 22, as will be described below in connection with FIG. 2.

The sensor unit 18 is here designed for the purpose of re-cording an optical, electrical, geometric or other biological, chemical or physical cell parameter and reporting said parameter to the process control and data processing 28 which then appropriately addresses the positioning unit 21 and/or the contacting and measuring unit 22 when the cell which has been found suitable on the basis of its parameter has reached the region of the contacting and measuring unit 22, due to the known transport flow 26.

The contacting and measuring unit 22 is designed as a microstructured part using microsystems technology and thus has very small dimensions.

Figure 2:
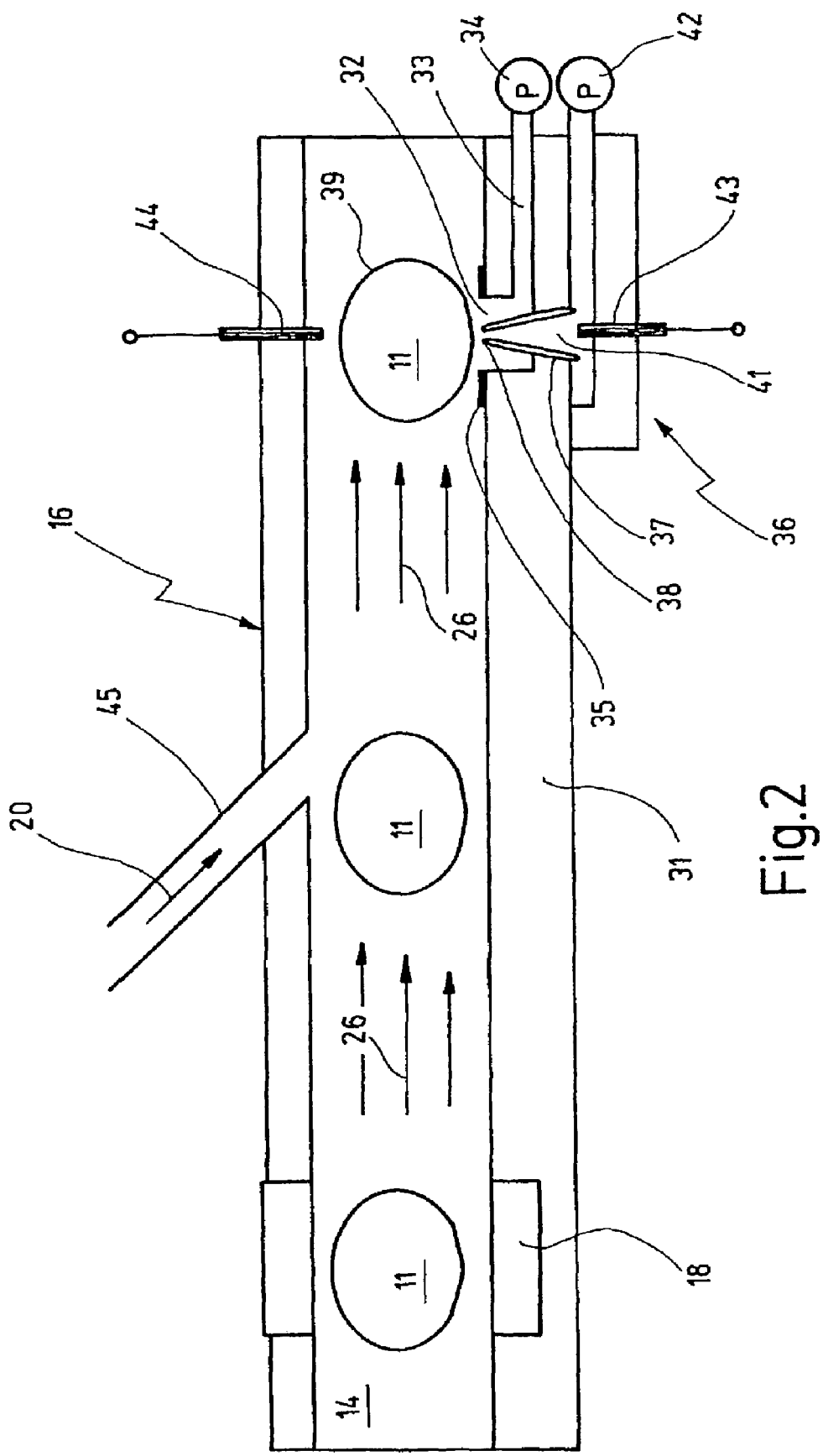
FIG. 2 depicts an enlarged representation of a section of the apparatus of FIG. 1 in the region of the contacting and measuring unit.

FIG. 2 depicts a section of the apparatus 10 of FIG. 1 on a larger scale and in diagrammatic side view. The flow channel 16 has a wall in the form of a substrate 31 in which an opening 32 is provided on which a cell 11 to be contacted is positioned. A suction channel 33 ends in opening 32, which suction channel is connected to a pump 34 via which a hydrodynamic pressure can be set in the opening 32 in order to suck in a cell 11.

A functional coating 35 which serves to immobilize a cell 11 in addition to the suction channel 33 is arranged on the substrate 31 around the opening 32, facing the cell 11. Once the cell 11 has been positioned on the opening 32, the low pressure of pump 34 is switched off so that the cell 11 only adheres to the functional coating 35 if it is attracted to said coating, and is otherwise washed away by the transport flow 26. The pump 34, however, is then switched on again for the actual measurement so that the cell 11 is securely immobilized on the opening 32.

Thus, the first positioning on the opening 32 merely serves to test whether the cell 11 is attracted to the functional coating 35 which provides chemical immobilization or immobilization via antibodies immobilized themselves. The functional coating 35 may also be a magnetic coating which arrests antibodies coupled to magnetic particles, which themselves are located on the cell 11.

This first positioning of the cell 11 on the opening 32 may also be carried out via the positioning unit 21 of FIG. 1, rather than by the suction channel 33.

A detachable contact unit 36 at which a replaceable con-tact tip 37 is arranged is located on the substrate 31, away from the cell 11. The top end 38 of the contact tip 37 bears against a cell membrane 39 of the cell 11, which membrane bulges slightly inward as a result.

A contact channel 41 runs through the contact tip 37 and ends at the top part 38 of said contact tip 37. At the other end, the contact channel 41 is connected to a pump 42 via which a hydrodynamic low pressure can be adjusted.

An electrode 43 which is electrically connected to the cell membrane 39 via electrically conductive liquid present in the contact channel 41 projects into said contact channel 41. A suitable counter electrode is a reference electrode 44 which projects into the flow channel 16 in the region of the opening 32.

The suction channel 33 not only immobilizes the cell 11 on the opening 32 but also presses its cell membrane 39 against the top end 38 of the contact tip 37, while contacting takes place, as in the conventional patch clamp technique, by applying a slight low pressure in the contact channel 41. If a pressure pulse is generated in the contact channel 41, the membrane patch circumscribed by the contact tip 37 is perforated, thus enabling intracellular measurements and stimulations.

A perfusion channel 45 also ends in the flow channel 16, through which a perfusion solution 20 can be directed to the immobilized and contacted cell 11, in order for test substances to flow around said cell and to measure the reaction of the cell 11 to said test substances.

Figure 3:
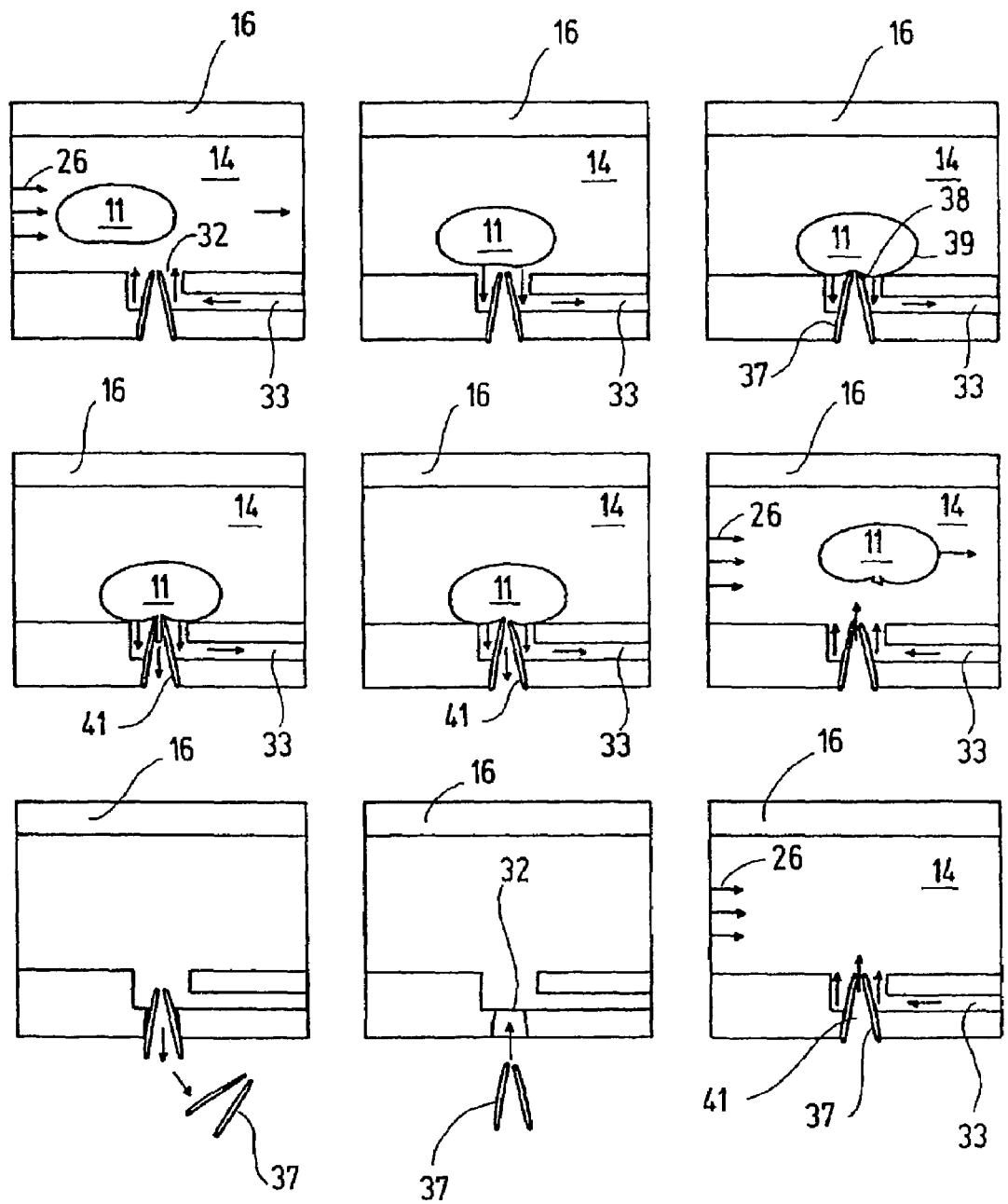
FIG. 3 depicts the diagrammatic course of electrically contacting a cell and replacing the contact tip.

A diagrammatic image sequence in FIG. 3 depicts the process of contacting and measuring/stimulating a cell 11.

In the first image in the top row, a liquid 14 which carries along a cell 11 flows through the flow channel 16. Like-wise, liquid 14 flows through the suction channel 33 into the interior of the flow channel 16.

When the cell 11 has reached the region of the opening 32, a hydrodynamic low pressure is generated via the suction channel 33 so that the cell 11 is sucked to the opening 32, as depicted in the second image of the first row.

The last image of the first row depicts the cell 11 with its membrane 39 bulged inward coming to rest on the top end 38 of the contact tip 37, as is also the case in the classical patch clamp technique. In contrast to the classical technique, however, contacting in the novel apparatus and the novel method takes place by the cell 11 being transported to the contact tip and automatically being immobilized there and being pressed onto the contact tip 37.

The first image in the second row indicates that a low pressure is applied to the contact channel 41 so as to contact the immobilized cell in the usual patch clamp technique manner. If the low pressure in the contact channel is increased in a pulse-like manner, the membrane patch is ruptured, making possible an intracellular measurement, as depicted in the second image of the second row. The combination of sucking pressure in the suction channel 33 and contact low pressure in the con-tact channel 41 results in a gigaseal between cell membrane 39 and top end 38 of the contact tip 37, as in the classical patch clamp technique. However, the gigaseal here is formed between the cell membrane 39 and the small area of the top end 38 and not a large support area, as is the case in DE 198 27 957 A1 mentioned at the beginning.

After measuring/stimulation has finished, the low pressure in the contact channel 41 is switched off and a high pressure is applied in the suction channel 43 so that the cell 11 is released again into the transport flow 26 which removes it.

The left image in the third row indicates that the contact tip is then removed from the opening 32 and a new contact tip 37 is put in, as indicated in the second image of the third row.

After the contact tip 37 has been replaced, the flow channel 16 and the suction channel 33 and the contact channel 41 are first flushed with liquid in order to prepare the system for contacting a new cell 11.

The contact tip is exchanged automatically by means of a micromanipulator so that it is possible, using the novel apparatus 10, to contact and measure/stimulate a multiplicity of cells in an automated and sequential manner.

Figure 4:
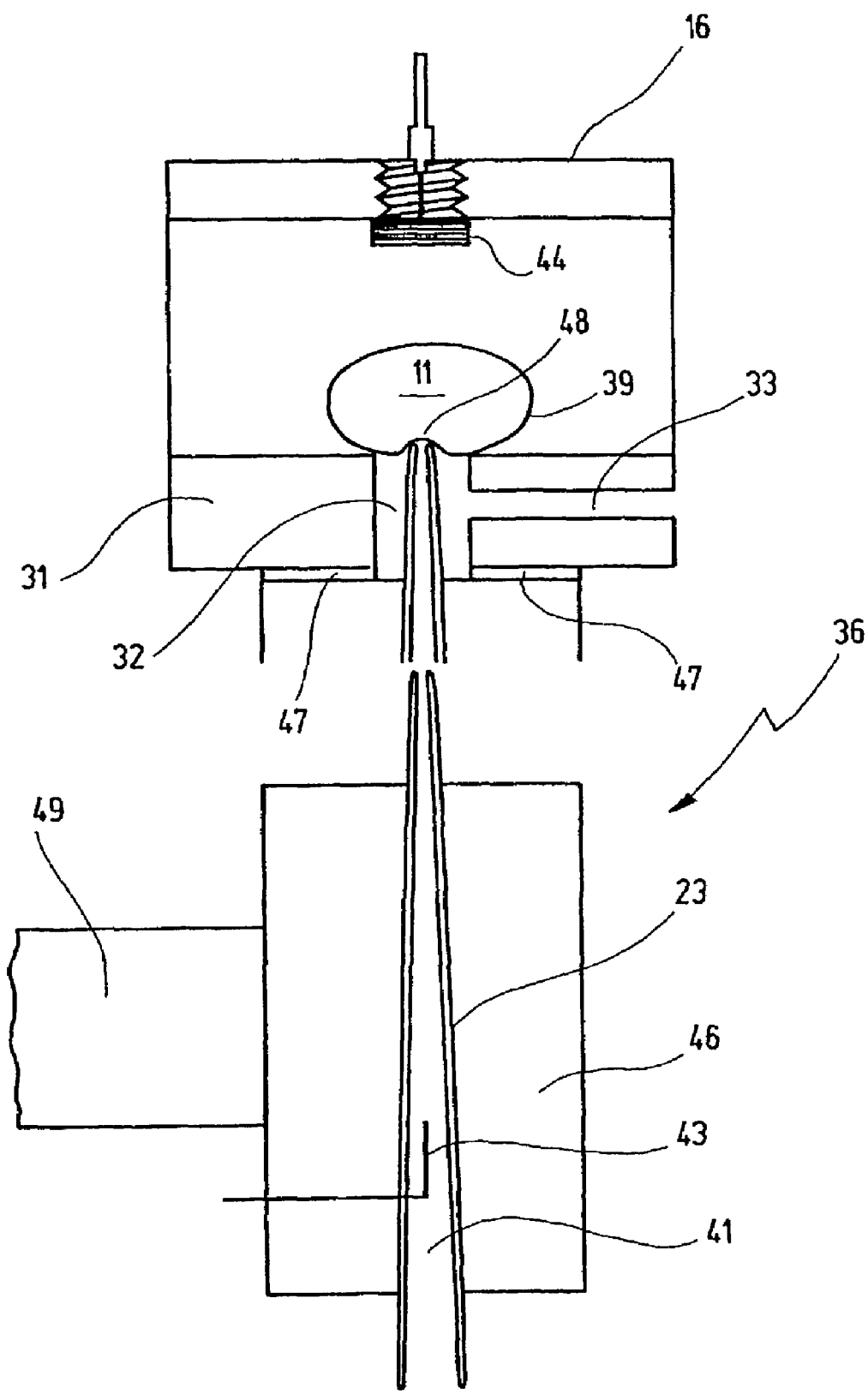
FIG. 4 depicts a first exemplary embodiment of a replaceable contact tip in which the suction channel is arranged in the substrate.

FIG. 4 depicts a first, very simply constructed exemplary embodiment of a replaceable contact tip 37.

In the exemplary embodiment shown, the contact tip is a conventional patch clamp tip 23 as is known already from FIG. 1. The patch clamp tip 23 is embedded in a plastic block 46 which is pressed from the outside against the substrate 31 so that the patch clamp tip 23 projects into the opening 32. Sealants 47 which are preferably prepared using Sylgard™ seal the opening 32 on the outside in a liquid-tight manner.

In the exemplary embodiment shown, the patch clamp tip 23 projects slightly past the substrate 31 into the flow channel 16 so that the cell membrane 39 of a cell 11 sucked and pressed onto the opening via the suction channel 33 bulges as indicated at 48, which is also the case in the patch clamp technique carried out manually.

The top image in FIG. 4 depicts the plastic block 46 bearing against the flow channel 16, while the bottom image depicts the plastic block 46 with an electrode 43 arranged in the con-tact channel 41. A micromanipulator which is depicted only diagrammatically acts on the plastic block 46. Said micro-manipulator 49 presses the plastic block 45 against the substrate 31 and arrests the plastic block 46 with pressure against the substrate 31, resulting in the already mentioned liquid-tight sealing.

The contact unit 36 shown in FIG. 4 is constructed in a very simple manner and essentially consists of a conventional patch clamp tip 23 which has been embedded into the plastic block 46.

Figure 5:
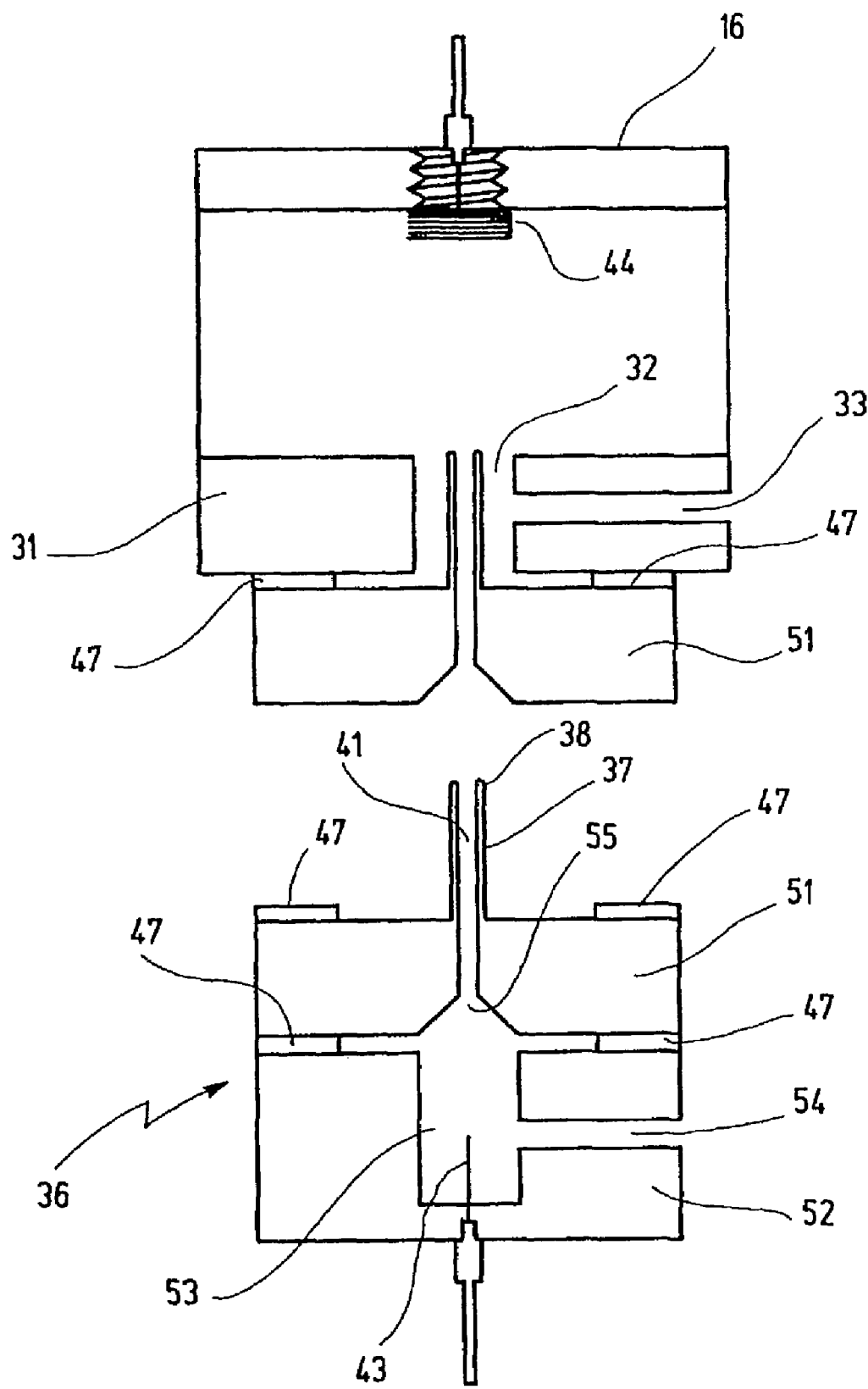
FIG. 5 depicts an exemplary embodiment like that of FIG. 4, in which, however, the contact unit is divided into a replaceable top part and a reusable bottom part.

FIG. 5 depicts another exemplary embodiment of a contact unit 36. The contact unit 36 of FIG. 5 has a top part 51 to be replaced and a reusable bottom part 52. The contact tip 37 with the contact channel 41 is arranged on the top part 51, with a chamber 53 into which the electrode 43 projects being provided in the bottom part 52. A first section 54 of the contact channel 41 whose second, funnel-shaped section 55 is arranged in the top part 51 likewise leads into the chamber 53.

The sealants 47 known already from FIG. 4 are located between top part 51 and bottom part 52 and are also arranged between top part 51 and substrate 31.

The contact unit 36 of FIG. 5 has a very simple construction and can be readily positioned, and replacing the contact tip 37 merely requires replacing the top part 51.

To this end, the entire contact unit 36 is removed from the substrate 31 using a micromanipulator, followed by replacing the top part 51 and again pressing the bottom part 52 with a new top part 51 against the substrate 31. This replacing may be automated, resulting in noticeable time-savings compared to manual replacement.

Figure 6:
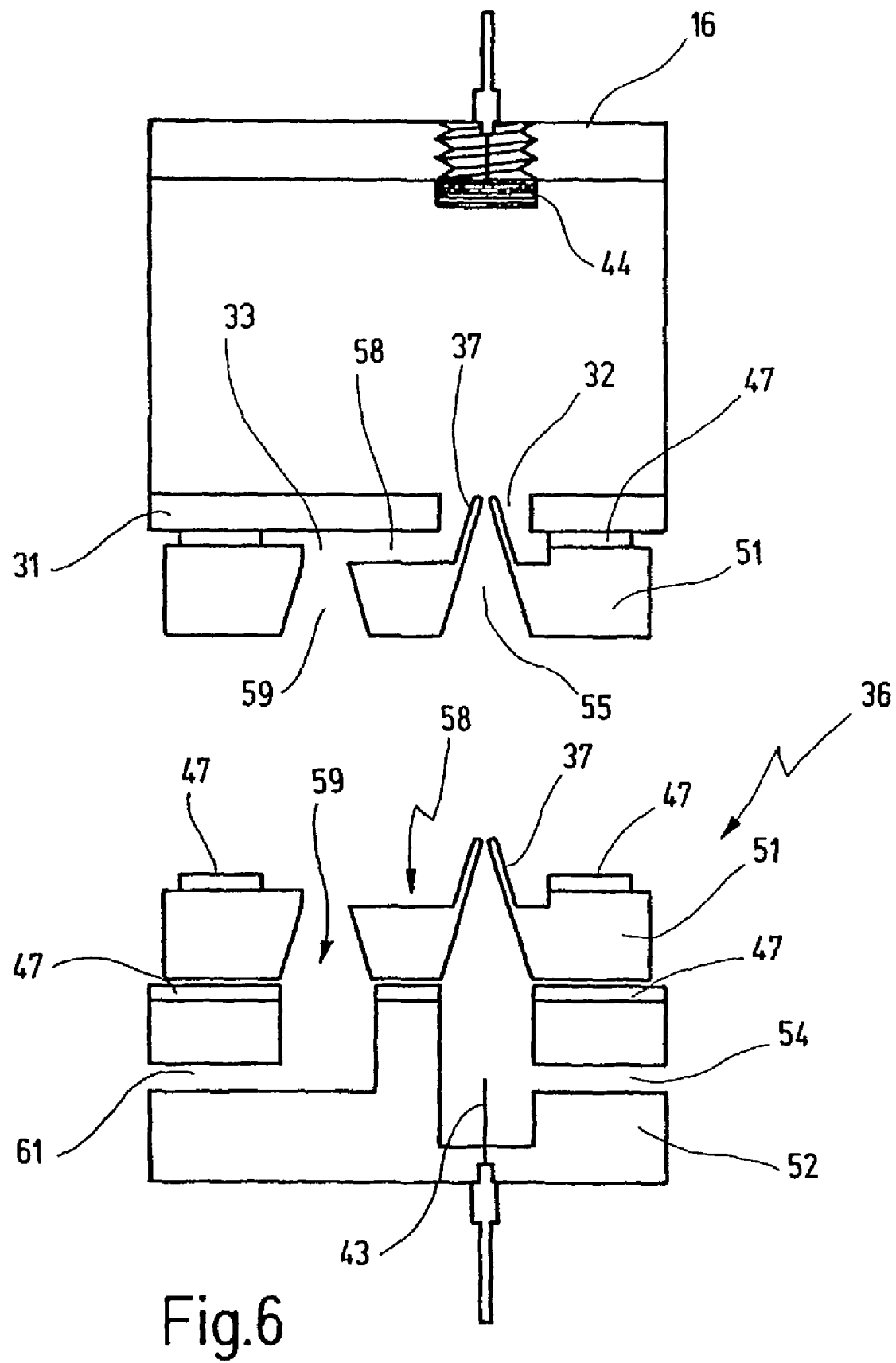
FIG. 6 depicts a contact unit like that in FIG. 5, but the suction channel is located in the contact unit.

In the exemplary embodiment of the contact unit 36 of FIG. 6, an annular space 58 which surrounds the contact tip 37 is located between the top part 51 and the substrate 31. The annular space 58 leads via an aperture 59 in the top part 51 to a first section 61 of the suction channel 33, which is also arranged in the contact unit 36 in this exemplary embodiment.

When the top part 51 has been pressed against the substrate 31, by pressing the bottom part 52 against the top part 51, the already known sealants 47 again provide liquid-tight sealing.

In the exemplary embodiment according to FIG. 6 all hydro-dynamic connections are provided in the bottom part 52, and the suction channel 33 ends in the opening in the known manner.

Figure 7:
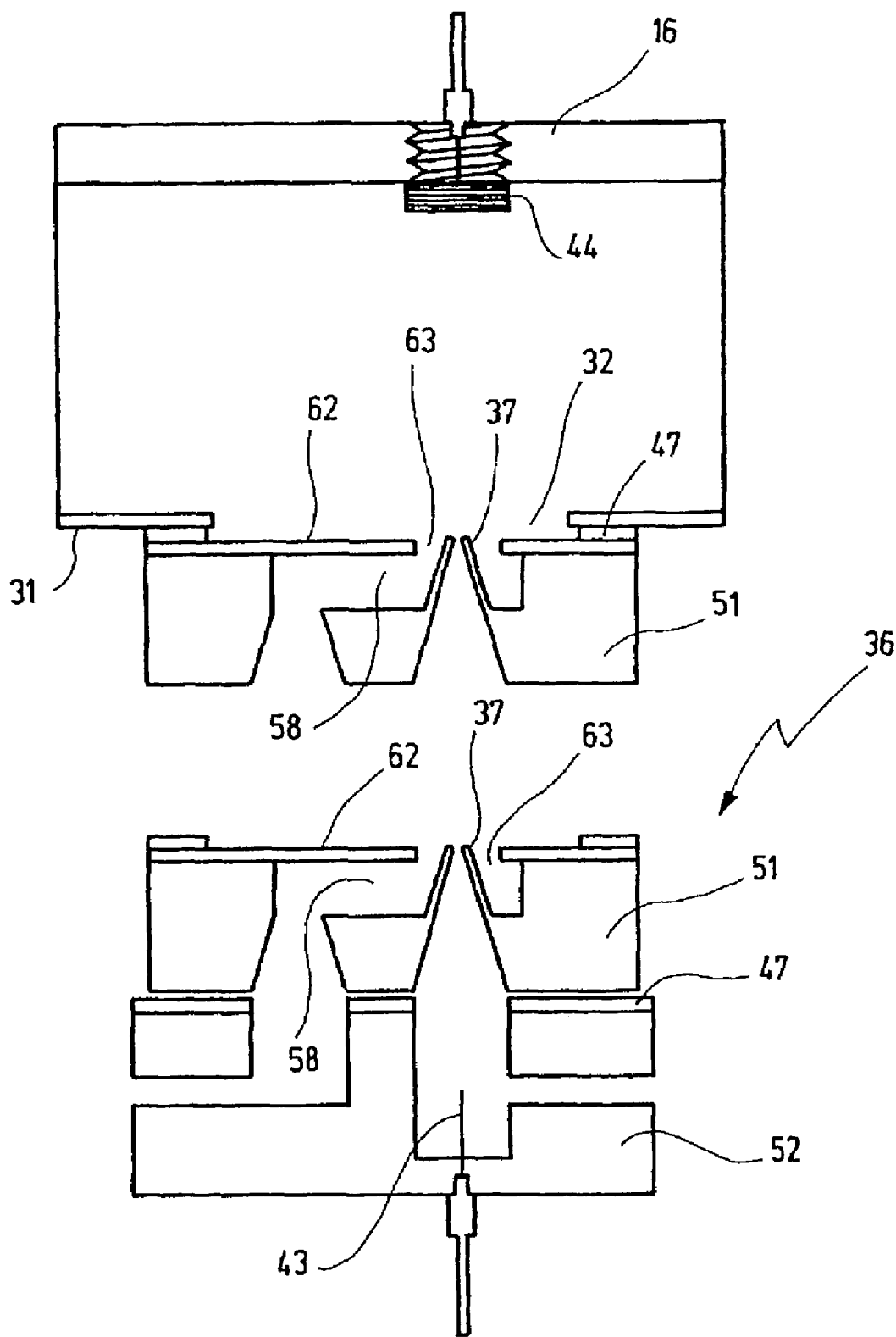
FIG. 7 depicts a contact unit like that in FIG. 6, but with a larger opening in the substrate.

Compared to the exemplary embodiment of FIG. 6, the annular channel 58 in the exemplary embodiment for the contact unit 36 in FIG. 7 is sealed to the substrate 31 which is very thin here by a membrane 62 which forms a gap 63 around the contact tip 37.

Compared to FIG. 6, the opening 32 in the substrate 31 is considerably larger so that the contact unit 36 can be positioned very easily at the substrate 31. Beyond that, the con-tact unit 36 of FIG. 7 corresponds to the contact unit 36 of FIG. 6.

What is claimed is:

1. An apparatus for electrically contacting biological cells suspended in a liquid, said apparatus comprising:
   a substrate having at least one opening,
   a suction channel ending in said opening, said suction channel being adapted to provide a first hydrodynamic low pressure at the opening for immobilizing a cell having a cell membrane on top of said opening,
   a contact unit being arranged below the opening and comprising a contact tip, and
   at least one electrode for electrically contacting the cell when it is immobilized on top of said opening,
   wherein the contact tip comprises a top end projecting into said opening in such a way that said contact tip comes to bear against the cell membrane when the cell is immobilized on top of said opening, and further comprises a contact channel which opens at the top end in such a way that a second hydro-dynamic low pressure can be exerted upon the cell membrane, and
   wherein the electrode is arranged within said contact channel, and
   wherein the contact unit has a replaceable top part comprising the contact tip and a reusable bottom part comprising the electrode and a first section of the contact channel,
   wherein the top part further comprises an annular recess formed around the contact tip and facing the substrate, with the annular recess having a passage connected to the suction channel.

2. The apparatus of claim 1, wherein the annular recess is covered by a membrane having a gap which surrounds the contact tip at a distance.

3. The apparatus of claim 2, wherein the membrane is fixed to the top part.

4. The apparatus of claim 1, further comprising a reference electrode projecting into the liquid in the vicinity of the opening.

5. The apparatus of claim 1, further comprising a functional coating provided on the substrate around the opening for immobilizing the cells on said opening.

6. The apparatus of claim 5, wherein the functional coating is selected from the group of: polyanions, polycations, polyethyleneimine, antibodies against cell surface molecules, and magnetic coating.

7. The apparatus of claim 1, further comprising a positioning unit for positioning a cell above the opening.

8. The apparatus of claim 7, wherein the positioning unit comprises one of the following: laser tweezers, a means for building up an electromagnetic field, or a means for generating a hydrodynamic force.

9. The apparatus of claim 1, further comprising a flow channel adapted to direct the liquid to the opening with a predefined transport flow.

10. The apparatus of claim 9, further comprising a microperfusion unit connected to the flow channel upstream of the opening for applying test substances to an immobilized cell.

* * * * *